(12) United States Patent
Brill et al.

(10) Patent No.: US 7,292,341 B2
(45) Date of Patent: Nov. 6, 2007

(54) OPTICAL SYSTEM OPERATING WITH VARIABLE ANGLE OF INCIDENCE

(75) Inventors: Boaz Brill, Rehovot (IL); Moshe Finarov, Rehovot (IL); David Scheiner, Yehuda (IL)

(73) Assignee: Nova Measuring Instruments Ltd., Rehovot (IL)

( * ) Notice: Subject to any disclaimer, the term of this patent is extended or adjusted under 35 U.S.C. 154(b) by 272 days.

(21) Appl. No.: 10/525,568

(22) PCT Filed: May 8, 2003

(86) PCT No.: PCT/IL03/00373

§ 371 (c)(1),
(2), (4) Date: Feb. 25, 2005

(87) PCT Pub. No.: WO03/095993

PCT Pub. Date: Nov. 20, 2003

(65) Prior Publication Data

US 2006/0001883 A1     Jan. 5, 2006

(30) Foreign Application Priority Data

May 9, 2002  (IL) .................................. 149557

(51) Int. Cl.
*G01N 21/55* (2006.01)
*G01N 21/00* (2006.01)

(52) U.S. Cl. .................................. 356/445; 356/237.2

(58) Field of Classification Search ............... None
See application file for complete search history.

(56) References Cited

U.S. PATENT DOCUMENTS

| 3,825,351 | A | * | 7/1974 | Seki et al. ............... 356/431 |
| 3,909,602 | A | * | 9/1975 | Micka ...................... 716/4 |
| 5,048,970 | A | | 9/1991 | Milosevic et al. |
| 5,106,196 | A | * | 4/1992 | Brierley .................. 356/445 |
| 5,392,125 | A | | 2/1995 | Reisser |
| 5,424,838 | A | * | 6/1995 | Siu ........................ 356/394 |
| 6,128,093 | A | * | 10/2000 | Niikura ................... 356/432 |
| 6,449,037 | B2 | * | 9/2002 | Jun et al. ............... 356/237.4 |
| 6,603,542 | B1 | * | 8/2003 | Chase et al. ........... 356/237.4 |
| 6,724,475 | B2 | | 4/2004 | Benesch et al. |

\* cited by examiner

*Primary Examiner*—Michael P. Stafira
(74) *Attorney, Agent, or Firm*—Dekel Patent Ltd.; David Klein (57) ABSTRACT

An optical system for use in measurements in a sample comprising a light source (102) operable to produce an incident light beam propagating in a certain direction towards the sample (S) through an illumination channel (IC), a detector unit (104) for collecting light coming from the sample through a detection channel (DC), and generating data indicative of the collected light, a light directing assembly (106) operable to direct the incident beam onto a certain location on the sample's plane with a plurality of incident angles, and to direct light returned from the illuminated location to the detector unit (104), the light directing assembly (106) comprising a plurality of beam deflector elements (108 A-D), at least one of the deflector elements being movable and position of said at least one movable deflector element defining one of the selected incident angles.

3 Claims, 6 Drawing Sheets

OPTICAL SYSTEM OPERATING WITH VARIABLE ANGLE OF INCIDENCE

FIELD OF THE INVENTION

The present invention is generally in the field of optical monitoring/inspection techniques, and relates to a spectrometer method and system.

BACKGROUND OF THE INVENTION

Spectrometer-based techniques, such as spectrophotometry and spectral ellipsometry, are widely used in microelectronics for measuring thin film properties and line profiles. An object to be measured may be a site on a semiconductor wafer (multi-layer stack) that may have with uniform thin-film structure, or may be patterned, e.g., line array in at least one layer of the multi-layer stack. If wavelength of incident light is of the order of the line array period, reflected light is zero-order diffracted light, while higher orders are scattered in different directions and do not reach an optical detector oriented to be capable of detecting the reflected light (scatterometry). For both the specular reflection and zero-order diffraction, the light used for measurements may be polarized. Measurement schemes may be of the kind based on measuring intensity of light (spectrophotometry) or polarization changes (ellipsometry).

An object under measurements, either of uniform or patterned structure may thus be described by an optical model with a set of parameters, such as optical constants, thickness of each layer, pattern geometry and profile. Measurement of a single spectrum is usually incapable of determining more than two-three unknown parameters of this set with high accuracy and high level of confidence. Hence, if more parameters of the optical model of a measured structure are unknown and are to be simultaneously determined from spectral measurements, more such measurements are to be independently carried out. The known approaches to increase the number of independent measurements (applicable for both the spectrophotometry and ellipsometry) are generally based on the following:

1. Step-by-step removal and measurements of the same stack downward to the substrate layer. Although this approach enables as many independent measurements as needed, it is destructive and is hard to implement for measuring wafers in production.

2. Step-by-step deposition and measurements of the stack layers. This approach provides a required number of measurements, but is timely consuming.

3. Individual deposition of each or some critical layers on a substrate and separate measurements of each of these layers. By this, measurements in a simple single-layer structure allows for determining both the optical properties and thickness of the single layer. The single-layer measured parameters can then be excluded from unknown parameters of the whole stack. This technique is also time consuming, requires a large number of test wafers, and does not takes into consideration the fact that the optical properties of a specific layer may be different when the layer is a part of a multi-layer stack, and therefore does not provide confident information.

4. Applying measurements to the same wafer in different ambiences, e.g., in air and in water, etc. This technique provides more information about the wafer, but a different ambience might cause some chemical changes of the wafer's top layer, such as photoresist.

Figure 1:
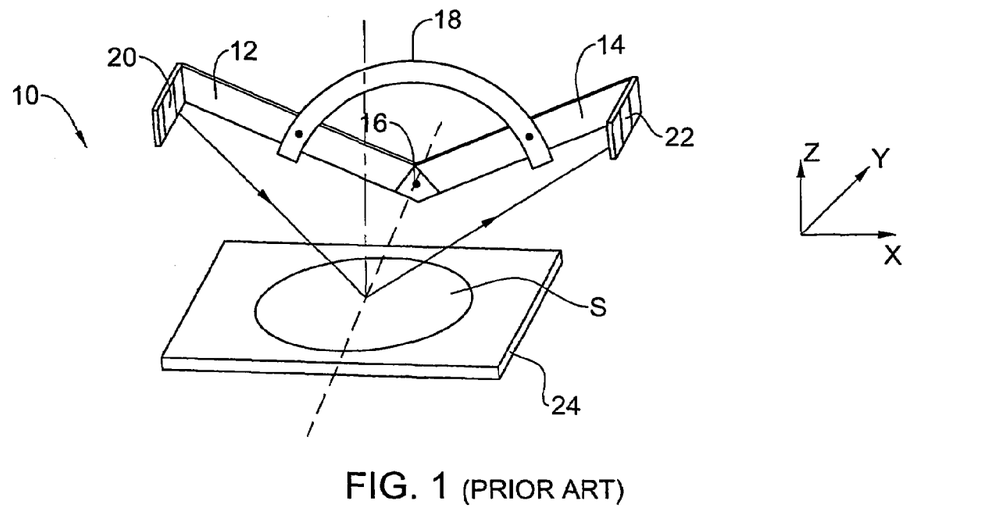
FIG. 1 is a schematic illustration of the prior art multi-angle optical system.

5. Measurements of the same site on a wafer with different angles of light incidence. FIG. 1 schematically illustrates such a variable angle measurement system 10, for example the H-VASE model commercially available from J.A. Woolam Co., Inc. The system has two arms 12 and 14 mounted for pivotal movement about a pivot axis 16 along a curved frame 18. The arms 12 and 14 are L-shaped and carry a light source 20 and a detector 22, respectively. In order to cover the entire surface of a wafer W, the latter is supported on a movable X-Y stage 24, which preferably is also Z-adjustable. This approach provides more information than the single incident angle technique, but suffers from the following drawbacks:

- long measurement time, which while being acceptable for material characterization, is not acceptable for production;
- a measurement system of a large footprint and size, which does not complies with the requirements for a measurement system in production, e.g., integrated metrology system;
- requirement for a massive and rigid mechanical platform, in order to provide accurate changing of the angle of incidence that can hardly be used for integrated metrology.

SUMMARY OF THE INVENTION

There is accordingly a need in the art to facilitate optical measurements in a sample, especially a multi-layer structure, by providing a novel method and system operable with variable angles of illumination and light collection.

The present invention provides for varying the angle of incidence of light onto a specific location (site) on the sample and, optionally also for varying the angle of collection of light returned from this site. The system according to the invention requires neither movement of a light source nor of a light detector, but rather utilizes a light directing assembly having a plurality of deflector elements defining a plurality of incident angles. Interaction of an incident beam with a selected one of the deflector elements provides a selected angle of incidence of the beam onto the sample. Preferably, the plurality of deflector elements has deflector elements located in a detection channel as well, thereby enabling interaction of the returned beam with a selected deflector element and accordingly a selected angle of light collection by a detector unit.

There is thus provided according to one aspect of the present invention, an optical system for use in measurements in a sample, the system comprising:

(a) a light source operable to produce an incident light beam propagating in a certain direction towards the sample through an illumination channel;

(b) a detector unit for collecting light coming from the sample through a detection channel, and generating data indicative of the collected light;

(c) a light directing assembly operable to direct the incident beam onto a certain location on the sample's plane with a plurality of incident angles, and to direct light returned from the illuminated location to the detector unit, the light directing assembly comprising a plurality of beam deflector elements, at least one of the deflector elements being movable, a position of said at least one movable deflector element defining a selected one of the incident angles.

According to one embodiment of the invention, the plurality of the deflector elements has two arrays of the deflector elements, one array being located in the illumination channel and the other array being located in the detection channel. Each of the arrays may be formed by deflector elements arranged in a spaced-apart relationship along the respective channel, in which case the deflector elements may be planar mirrors with or without associated focusing lenses, at least one of the deflector elements being movable. Each of the arrays may be formed by a reflecting surface of a parabolic-sector mirror, in which case the light directing assembly preferably comprises at least one movable planar mirror in the illumination channel, and preferably also comprises a movable planar mirror in the detection channel. According to another embodiment of the invention, the plurality of deflector elements comprises a single parabolic-sector mirror that faces the sample's plane with its reflecting surface. In this case, the light directing assembly comprises planar mirrors, at least one being movable between a plurality of operative positions thereby defining the plurality of the incident angles.

According to another aspect of the present invention, there is provided, a method for measuring in a sample, the method comprising:

(i) providing an incident light beam propagating in a certain direction towards the sample along an illumination channel;

(ii) directing the incident beam onto a certain location on the sample's plane with a plurality of incident angles, said directing comprising deflecting the incident beam by a selected one of a plurality of deflector elements resulting in the selected one of the angles of incidence of the beam onto said certain location.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

FIG. 1 shows the prior art optical system capable of providing various angles of incidence of a light beam onto a sample.

Figure 2:
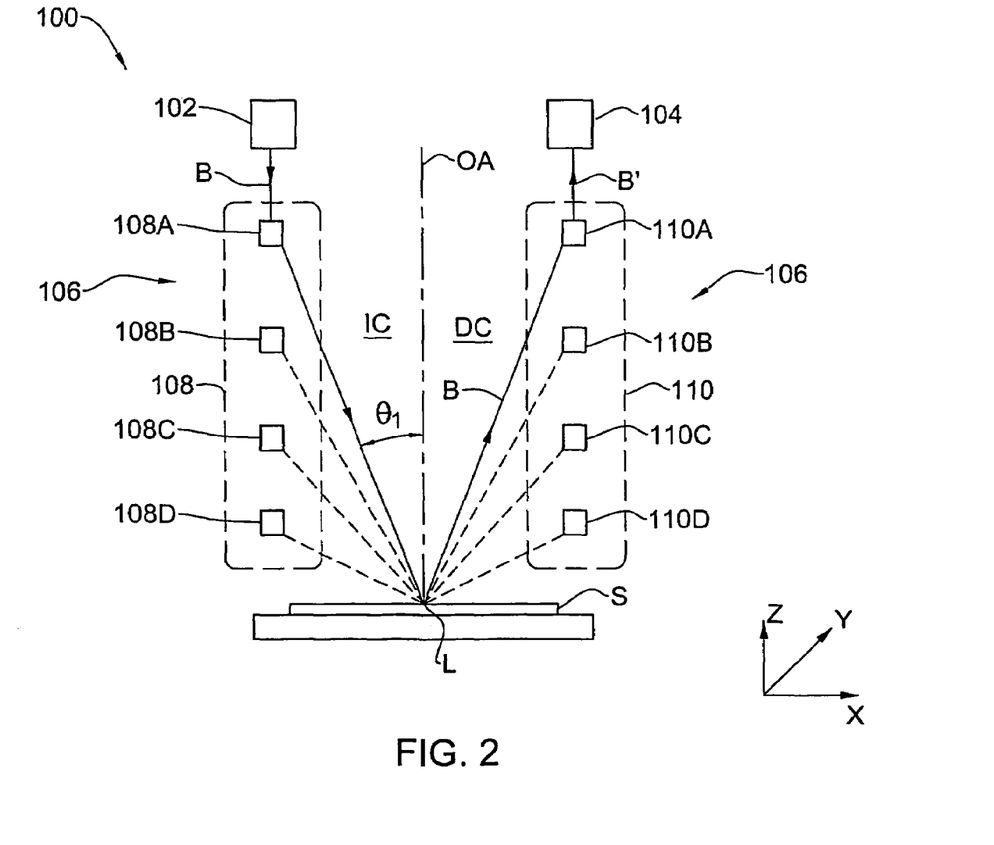
FIG. 2 is a schematic illustration of an optical system according to one embodiment of the invention.

Referring to FIG. 2, there is illustrated an optical system 100 according to one embodiment of the invention applied to a sample (e.g., wafer) S. The system 100 comprises such main constructional parts as a light source 102 (e.g., a Xe lamp) producing an incident light beam B, which in the present example propagates from the light source parallel to an axis OA normal to the sample's plane; a detector unit 104 (e.g., spectrophotometer); and a light directing assembly, generally at 106, comprising a plurality of deflector elements. Light beam B propagates through an illumination channel IC, impinges onto the sample at a location L, and returned light B' (reflected and/or scattered) propagates through a detection channel DC towards the detector 104. The sample is typically supported on a stage, and in order to measure/monitor a plurality of sample's sites a relative displacement between the sample and the optical system (at least deflector assembly) is provided, preferably by moving the stage with respect to the optical system. The stage may be of different types, i.e., x,y- or r,θ-movable stage for scanning the entire surface of the wafer, and z-movable for bringing the measurement site to the best focus of the optical system.

In the present example of FIG. 2, the plurality of deflector elements in the light directing assembly 106 has two arrays of deflector elements 108 and 110 located at both sides of the axis OA. The array 108 is associated with the light source 102 (illumination channel IC) and the array 110 is associated with the detector unit 104 (detection channel DC). Additionally, in the present example of FIG. 2, each of the arrays 108 and 110 has separate (discrete) deflector elements—four such elements 108A-108D and 110A-110D in the arrays 108 and 110, respectively, which are arranged in a spaced-apart relationship within the respective channel. All the deflector elements, except for the lowermost ones (closest to the sample's plane) 108D and 110D, are movable to be in and out of the optical path of the respective beam (incident or returned), e.g., are mounted for a reciprocating movement along X- or Y-axis. Generally speaking, each beam deflector element in the array can be in its operative state, in which it is in the path of the respective light beam, and can be in its inoperative state, in which it is out of the path of the respective beam. This can be implemented in different ways, namely, by reciprocating, rotating or pivotal movement of the element with respect to the path of the light beam propagation towards the element. When the selected one of the deflector elements is in the optical path of the light beam, all other elements are out of this path. For example, the deflector elements can be sequentially shifted between the two positions. This can be realized by locating the uppermost deflector element 108A in the path of the emitted beam B, thereby automatically preventing the beam interaction with the other elements 108B-108D, and providing the beam incidence onto the location L on the sample with a certain incident angle $\theta_1$. In this case, the deflector elements 110A-110D of the detection channel are arranged such that the deflector element 110A only is in the path of the specularly reflected beam B'. Then, the uppermost element 108A is shifted away from the axis OA, thereby automatically providing the incident beam deflection by the next element 108B, etc. It should be understood that in order to provide the operative state of a selected deflector element, not necessarily this selected element is to be moved, but rather one or more other elements of the deflector assembly, as will be exemplified further below.

As shown in FIG. 2, the incident beam interaction with a different one of the deflector elements 108A-108D results in a different angle of incidence of the beam B onto the same location (point) L on the sample. To this end, the deflector elements are differently oriented with respect to the axis OA. In the example of FIG. 2, variation of the angle of light collection (detection) is aimed at collecting only specular reflections of the incident beam. It should also be noted that the movable elements of the illumination and detection channels forming a pair with respect to the certain incident/collected angle, e.g., elements 108A and 110A, can be associated with a common drive.

The number of different angles of incidence/collection depends on the opto-mechanical design of the system 100. Practically, the provision of four-five angles is sufficient for most of the inspection/monitoring applications, enabling the system (including both the illumination and the detection channels) to be compact, up to the wafer size (200-300 mm).

Since each deflector element in the arrays of the illumination and detection channels can be separately aligned, a very high accuracy of alignment can be achieved, which enables to provide accurate location of the illumination spot (location L) on the chosen measurement site. During the alignment procedure, a nominal angle of incidence may be changed within a certain tolerance. However, accurate measurements require knowledge of each angle of incidence with high accuracy. This problem can be solved by using a calibration stage. This can for example be implemented in the following way. A known object is measured, e.g., $SiO_2$ layer on Si with the known thicknesses (commercially available from VLSI Standards Inc), and the actual angle of incidence is calculated by reaching the best fit between measured value of the film thickness in calibration standard parameters and its specified value.

It is typically desirable to set a measurement spot on the same place (x, y, z) on the wafer for all the angles of incidence, which is practically difficult to implement with the currently available alignment technique. To solve this problem, the coordinates (x, y, z) of the measurement spot may be determined for each incident angle separately by carrying out another calibration procedure. A calibration target in the form of a small mirror, e.g., chrome-on-glass mirror of a 50 μm diameter may be used. By changing x, y and z coordinates of the wafer supporting stage, a maximal signal of the returned light (reflection) is determined for each incident angle. This correction of coordinates ($\Delta x$, $\Delta y$ and $\Delta z$) is stored in the memory of the measurement system (a control unit). Thus, while changing the angle of incidence/collection by selecting a corresponding pair of the deflector elements, the position of the wafer stage is changed accordingly to compensate for $\Delta x$, $\Delta y$ and $\Delta z$ for this specific angle.

Figure 3A:
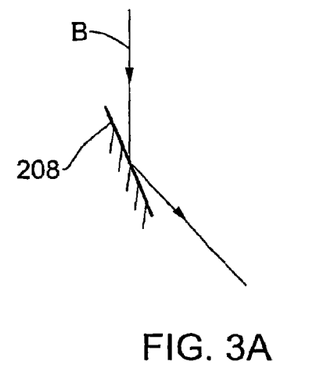
FIGS. 3A to 3D more specifically illustrate three possible examples, respectively, of a deflection element suitable to be used in the optical system of FIG. 2.
Figure 3B:
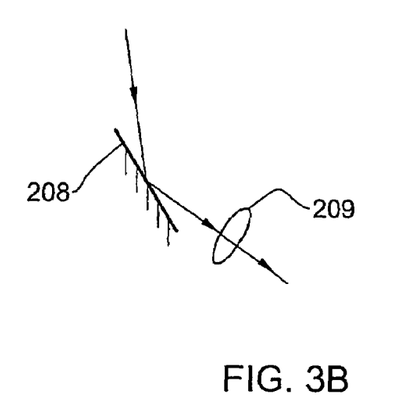
Figure 3C:
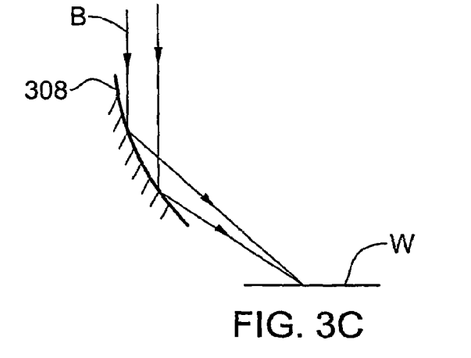
Figure 3D:
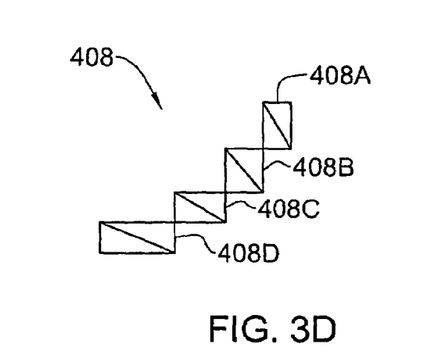

Reference is now made to FIGS. 3A-3D showing several examples of the configuration of the separate deflector elements suitable to be used in the system 100. In the example of FIG. 3A, the deflector element 208 has a planar reflecting surface (mirror), which may be associated with a lens 209 for beam focusing purposes, as shown in FIG. 3B. In the example of FIG. 3C, a deflector element 308 has a curved (concave) reflecting surface (preferably, a parabolic mirror) thereby providing both the deflection and focusing of the incident beam. As shown in FIG. 3D, a deflector assembly part 408 (associated with either illumination or detection channel) can be formed with discrete deflector elements 408A-408D supported in a step-like structure, so as to be moved together by a common drive (not shown). It should be noted that the deflector elements used in arrays of the illumination and detection channels are not necessarily of the same type, but may be of different types. For example, the illumination channel may include the curved mirrors, while the detection channel may include planar mirrors.

Figure 4:
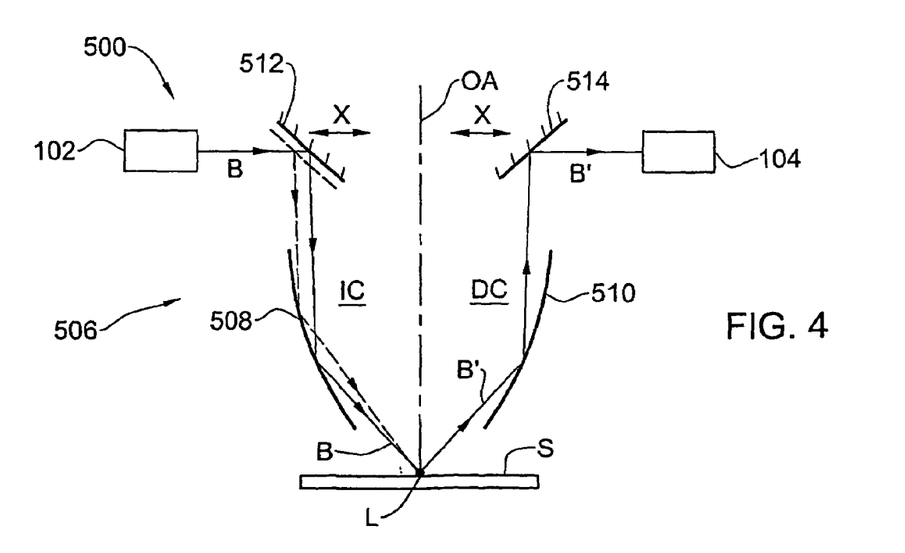
FIG. 4 schematically illustrates an optical system according to another embodiment of the invention.

FIG. 4 illustrates an optical system 500 according to another embodiment of the invention. To facilitate understanding, the same reference numbers are used for identifying components that are common in systems 100 and 500. In the system 500, the plurality of deflector elements in a light directing assembly 506 includes two symmetrical sectors 508 and 510 of a parabolic mirror accommodated in, respectively, illumination and detection channels and oriented such that the measurement site (location L) is located in the focal point of the mirror. Further provided in the light directing assembly 506 is a pair of movable planar mirrors 512 and 514 located in, respectively, illumination and detection channels IC and DC. In the present example, in distinction to the previously described ones, each of the continuous parabolic reflecting surfaces of the mirror sectors 508 and 510 presents an array of deflector elements (deflecting locations), providing a plurality of different angles of incidence/collection. In order to select a desired one of the incident angles, the mirror 512 is moved along the X-axis into a corresponding position with respect to the mirror sector 508. Similarly, in order to collect light returned from the sample with a desired angle (e.g., specular reflection), the mirror 514 is brought to a corresponding position along the X-axis. It should be understood that the provision of a continuous parabolic surface allows for obtaining the light response intensity (e.g., specular reflection) as a continuous function of angle of incidence.

Figure 5:
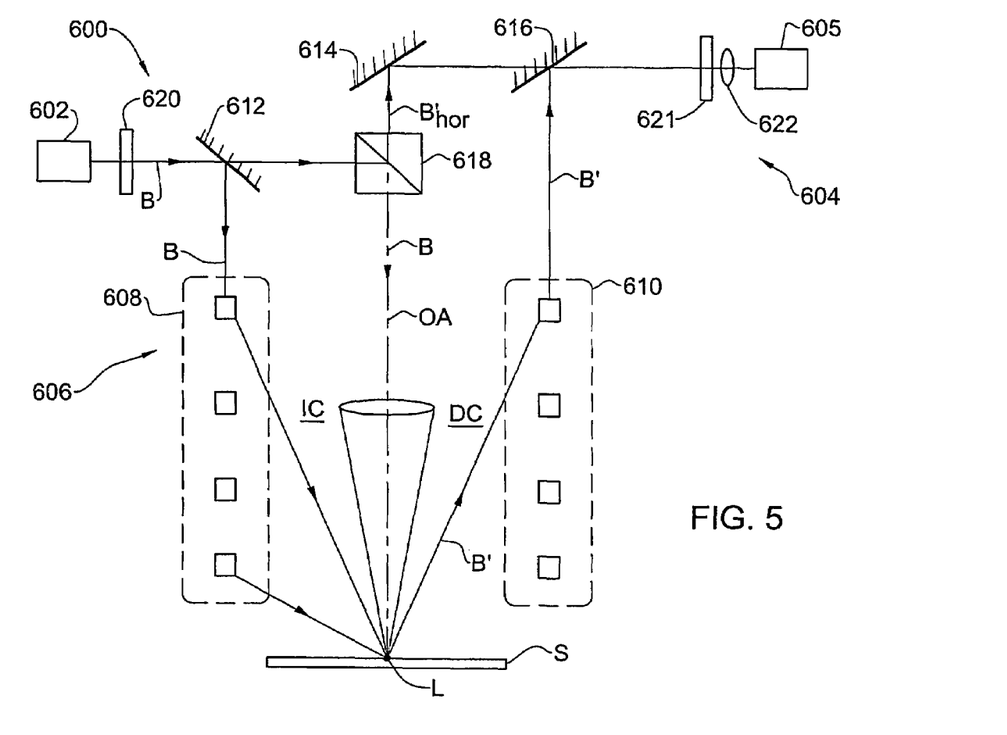
FIG. 5 is a schematic illustration of an optical system according to yet another embodiment of the invention, utilizing the multi-angle illumination/detection and also normal-incidence illumination/detection and/or imaging.

In the systems 100 (FIG. 2) and 500 (FIG. 4), multiple, non-zero angles of incidence of the beam onto the sample are utilized. FIG. 5 schematically illustrates how such a system can be easily modified in order to provide also measurement/monitoring of the sample with the normal incidence (zero-angle). A system 600 is shown having a light source 602, a detector unit 604, and a light directing assembly 606 comprising the plurality of deflector elements (including two arrays of deflector elements 608 and 610 in the present example), mirrors 612, 614 and 616, and a beam splitter 618. The detector unit 604 has a spectroscopic detector 605 and a tube lens 622. Optionally provided in the system 600 are polarizing elements 620 and 621 located, respectively, in the optical path of a light beam emitted by the light source 602 and a light beam propagating to the detector unit. Mirrors 612 and 616 are mounted for movement (e.g., rotation) between their operative and inoperative states.

When the mirrors 612 and 616 are in the operative state, i.e., in the path of the incident and reflected beams B and B', respectively, the multi-angle mode is realized. The beam B is reflected by the mirror 612 to propagate through the multi-angle illumination IC, thereby resulting in the beam incidence onto the sample with a certain non-zero angle of incidence, and the returned beam B' propagates through the multi-angle detection channel DC to be reflected by the mirror 616 to the detector unit 604. By shifting the mirrors 612 and 616 into their inoperative state, i.e., being out of the optical path of the beams B and B', the beam B is directed towards the beam splitter 618 to propagate through a normal illumination/detection channel IC'. The beam splitter 618 reflects the beam B to propagate to the sample along the axis OA through an objective lens OL. A specular reflection $B'_{nor}$ of the normal incident beam $B_{nor}$ propagates along the axis OA through the beam splitter 618, and is reflected by the mirror 614 to the detector unit 604.

Figure 6A:
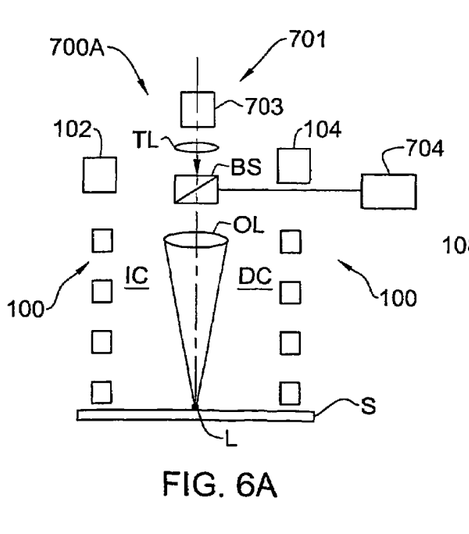
FIGS. 6A and 6B illustrate two more examples of using normal-incidence illumination/detection or imaging channel in the optical system of the invention.
Figure 6B:
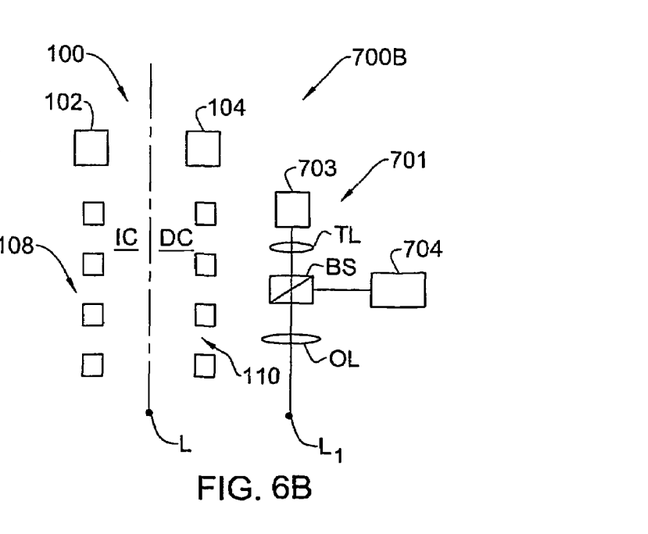

It should be understood that the normal incidence illumination/detection channel can utilize separate illuminator and detector, other than those used in the multi-angle illumination/detection system. This is schematically shown in FIGS. 6A and 6B. In the example of FIG. 6A, an optical system 700A has a multi-angle illumination/detection sub-system constructed similarly to the system 100 of FIG. 2, and a normal illumination/detection sub-system 701. The sub-system 701 has a light source 703, a detector 704, and a suitable optics including a beam splitter BS, an objective lens OL, and a tube lens TL, and is accommodated such that, in each relative location of the sample relative to the optical system 700A, the same site L is measured/monitored by both sub-systems 100 and 701A. An optical system 700B of FIG. 6B, similar to the system 700A, utilizes the sub-systems 100 and 701, but with the sub-system 701 being applied to a measurement site $L_1$ spaced-apart from the site L to which the sub-system 100 is applied. In this case, a relative distance between the sites L and $L_1$ is determined in a simple calibration procedure and stored in the system memory.

It should be understood that the normal incidence/detection sub-system 701 can be used as an imaging module, being a microscope with a CCD detector and suitable illumination and imaging optics. A control unit (not shown) of the system thus has an electronic card (frame grabber) for grabbing a video signal from the CCD, and an image processing software (including pattern recognition) for processing the grabbed signal. The pattern recognition software allows for identifying the measurement site and, in combined operation with X, Y, Z movable system (stage), allows for localizing the required measurement site in the measurement position (site L) as a point of intersection between the axes of the illumination and detection channels.

Figure 7A:
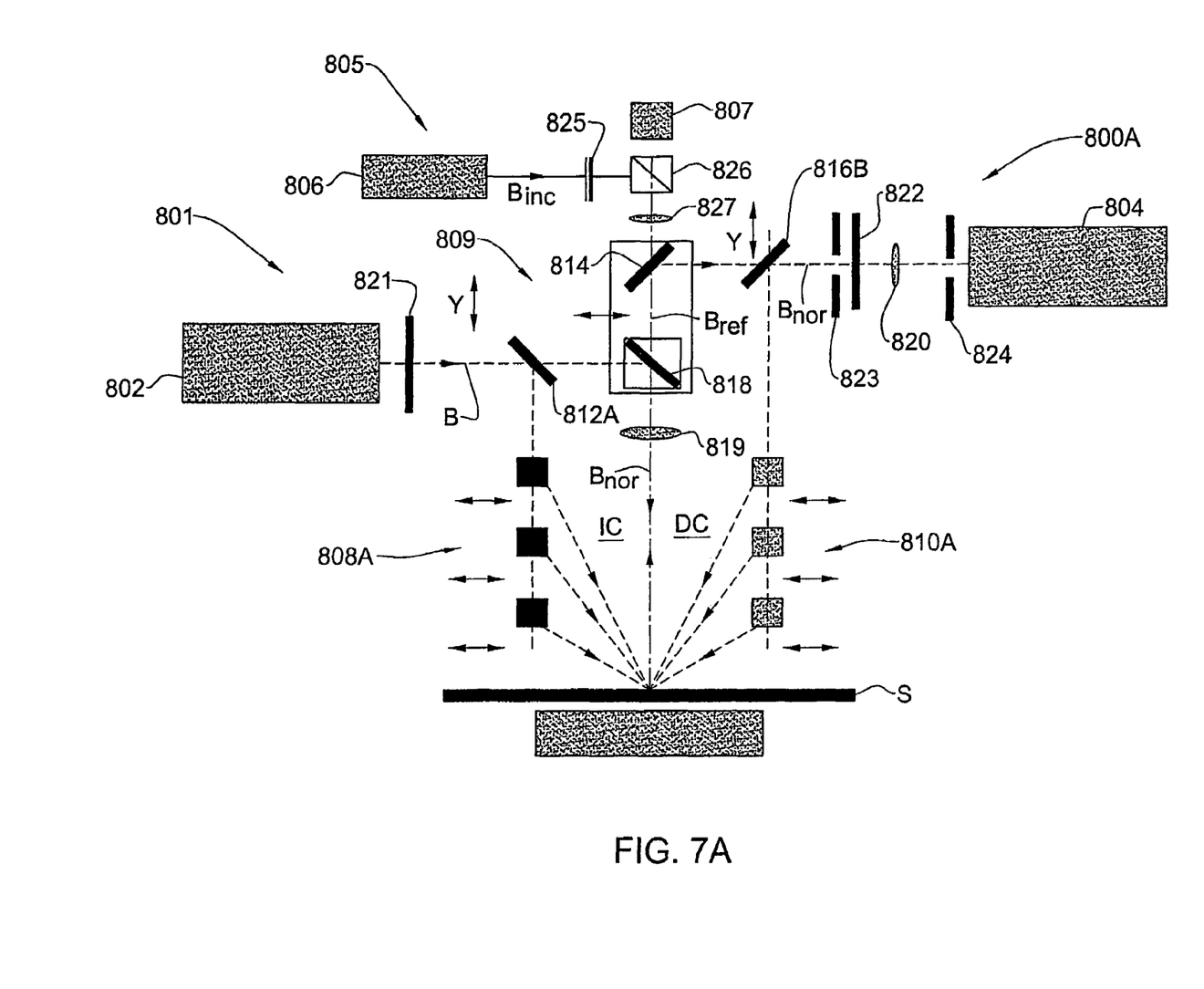
FIGS. 7A and 7B illustrate optical systems according to yet another examples of the invention designed for carrying out multi-angle and normal incidence measurement/monitoring, as well as imaging and auto-focusing functions.
Figure 7B:
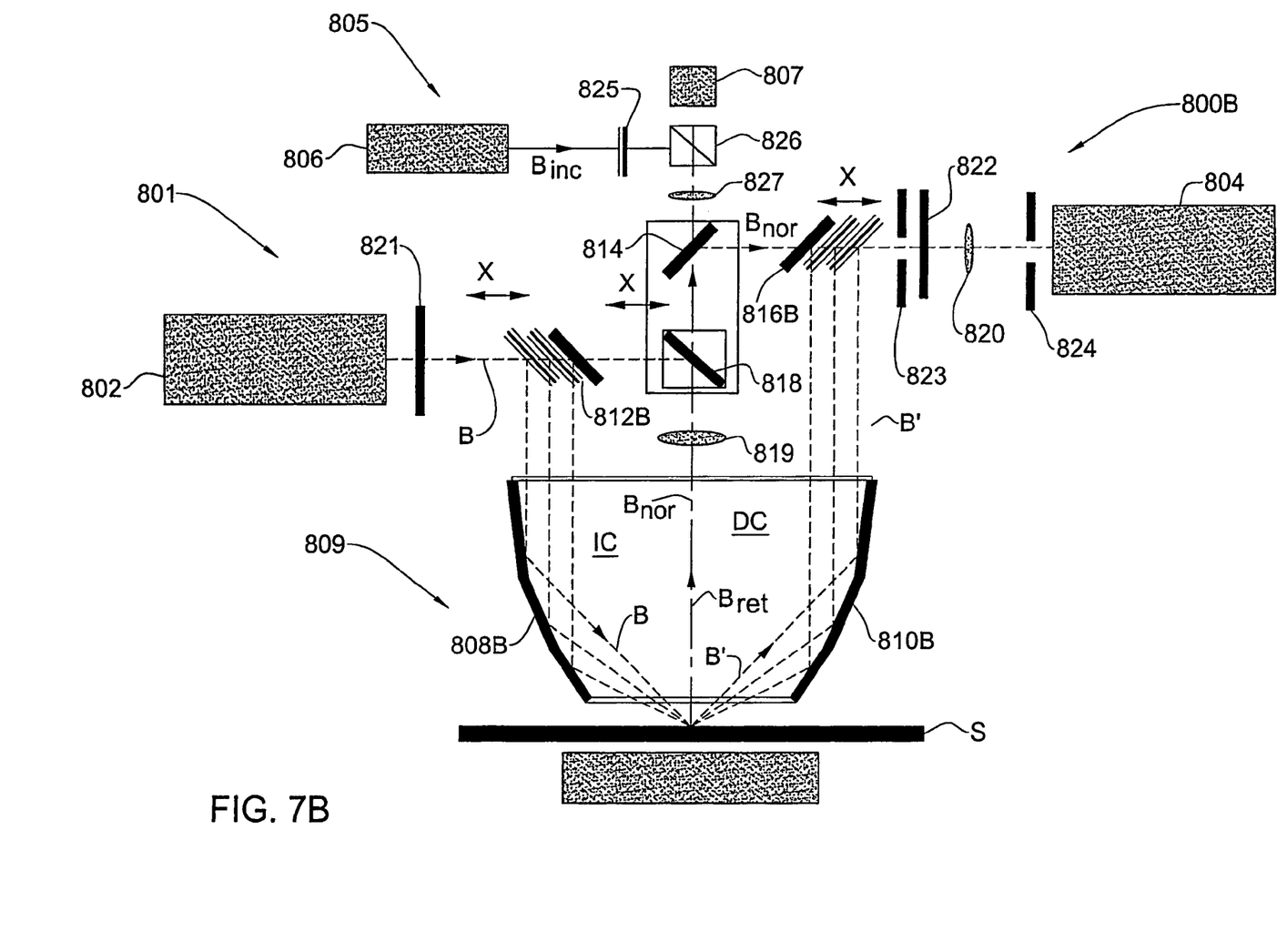

Reference is made to FIGS. 7A and 7B illustrating optical systems 800A and 800B, respectively, each designed for carrying out multi-angle and normal incidence measurement/monitoring, as well as imaging and auto-focusing functions. To facilitate understanding, the same reference numbers are used for identifying the similar components in the systems 800A and 800B. The systems differ from each other in that the pluralities of deflector elements of the systems 800A and 800B comprise, respectively, arrays of separate spaced-apart deflector elements (808A and 810A) and two continuous deflecting surfaces defining the arrays of deflector elements (808B and 810B).

Thus, the system 800A (and 800B) comprises a multi-angle and normal-incidence measurement sub-system 801 utilizing a light source 802 (e.g., a Xe lamp with appropriate optics) and a detector unit 804 (e.g. spectrophotometer based on grating and photo-diode array); and an imaging and auto-focusing sub-system 805 utilizing a light source 806 (QTH lamp with appropriate optics) and a detector unit 807 (including a CCD camera). The sub-system 801 further comprises a light directing assembly 809 including the plurality of deflector elements, mirrors 812A (or 812B in system 800B), 814 and 816A (or 816B in system 800B), a beam splitter 818, and objective and tube lenses 819 and 820. Preferably, the light directing assembly of the sub-system 801 also comprises polarizing elements 821 and 822. The detector unit 804 preferably also comprises an aperture stop 823 and a pinhole aperture 824. The aperture stop 823 is used for adjusting numerical aperture of the reflected light beam. The pinhole aperture 824 is used to limit a measured area on the wafer W.

In both systems 800A and 800B, each of the mirrors 812A (or 812B) and 816A (or 816B) is shiftable between its inoperative state (out of the optical path of the respective beam) and operative state (in the path of the respective beam) as described above with reference to FIG. 5. In the system 800A, at least some of the deflector elements in the arrays 808A and 810A are movable to provide operative and inoperative state of the selected deflector element in each array, while in the system 800B, the parabolic mirrors 808B and 810B are stationary mounted, and mirrors 812B and 816B are additionally movable along the X-axis between different operative positions thereof to thereby provide the operative state of the selected deflector element in the arrays (deflecting location).

When the mirrors 812A and 816A are in the operative state, a beam B from the light source 802 is directed to the sample through the multi-angle illumination channel IC (with only one deflector element in the array 808A being currently operative), and a reflection B' of the inclined incident beam B propagates through the multi-angle detection channel DC to the mirror 816B, which reflects the beam B' to the detector unit 804. When the mirrors 812A and 816B are inoperative, the beam B is reflected from the beam splitter 818 to normally impinge onto the same location L on the sample, and a reflection $B'_{nor}$ passes through the beam splitter 818, and is reflected by the mirror 814 to the detector 804.

The sub-assembly of the light directing assembly including the beam splitter 818 and mirror 814 is also movable (e.g., along the X- or Y-axis) between its operative and inoperative position to be, respectively, in and output of the optical path of the respective beams. When this sub-assembly is operative, the system 800A functions as described above, namely, carries out measurements with the sub-system 801. In order to operate the sub-system 805 to carry out pattern recognition and/or auto-focusing, the sub-assembly 818-814 is shifted into its inoperative state.

The sub-system 805 comprises a grid assembly 825, a beam splitter 826 for spatially separating incident and reflected beams $B_{inc}$ and $B_{ref}$, and a tube lens 827. There are several ways to reach the best focus. As shown in the figure, beam $B_{inc}$ passes through the grid assembly 825, is reflected by the beam splitter 826, and is focused onto the sample by the tube lens 827 and the objective lens 819. The reflected beam $B_{ref}$ propagates back to the CCD 804 through the beam splitter 826. The use of the grid assembly 825 is aimed at finding the best focus by analyzing the image of line arrays (grid) projected on the sample plane through the illumination channel. This technique is disclosed in U.S. Pat. No. 5,604,344 assigned to the assignee of the present application. Generally, another auto-focusing sensors may be applied as well.

Figure 8:
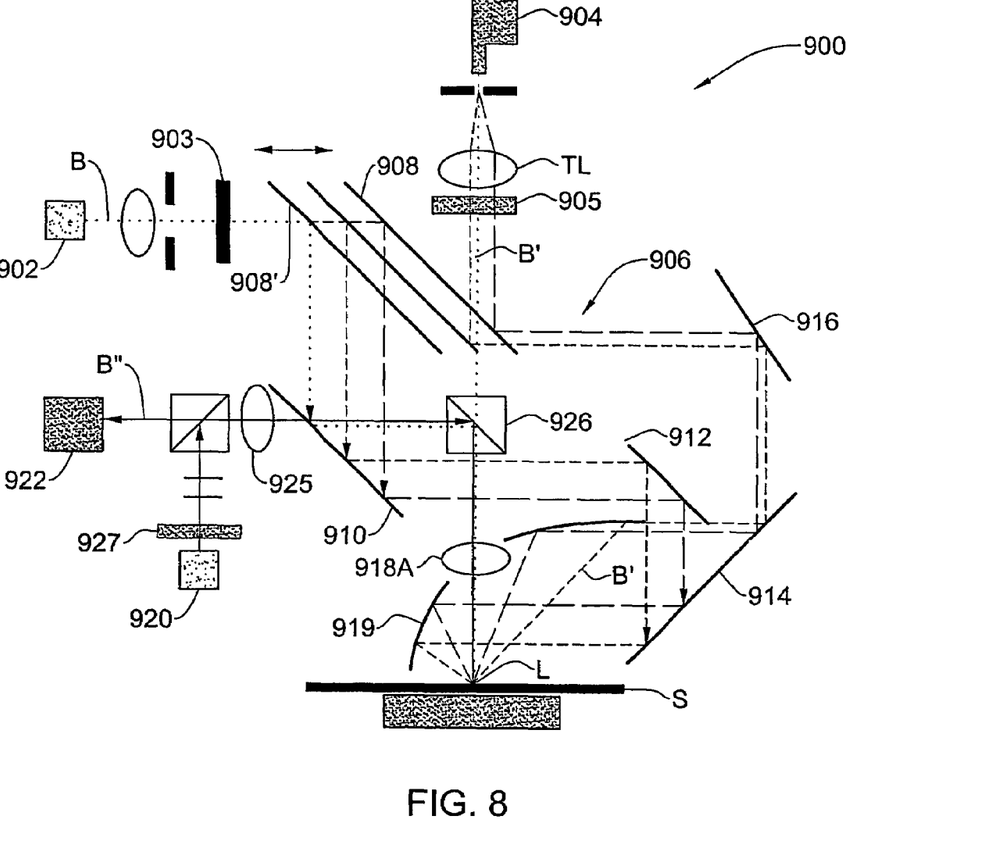
FIG. 8 is a schematic illustration of yet another embodiment of the invention, wherein a deflector assembly comprises a parabolic-sector mirror.

Turning now to FIG. 8, there is illustrated yet another embodiment of an optical system 900 according to the invention. The system 900 comprises a light source 902 optionally associated with a polarizing element 903; a detector unit 904 (e.g., including a spectrophotometer) also optionally associated with a polarizing element 905; and a light directing assembly 906. The light directing assembly 906 comprises a double-side movable planar mirror 908, a wavelength-selective beam combiner 910 (e.g., transparent for wavelength more than 750 nm and reflective for wavelengths up to 750 nm), three planar mirrors 912, 914 and 916, and a parabolic-sector mirror 918 whose continuous reflecting surface facing the sample's plane presents a plurality of deflector elements. The mirror 918 is formed with an opening 918A (generally, an optical window), where for example an objective lens 919 can be located. The provision of the optical window enables a normal incidence illumination/detection. The wavelength selectivity of the mirror 910 is optional and is associated with the provision of an imaging channel formed by an additional light source 920, an imaging detector unit 922 (e.g., CCD camera), a beam splitter 924 and a tube lens 925. It should be noted that the use of the additional light source 920 is optional, and the same light source 902 can be used in the imaging channel, in which case the mirror 908 is shifted into its extreme left position denoted 908'. Further provided in the light directing assembly is a beam splitter 926 serving for the normal incidence measurement, as well as for imaging purposes in this specific configuration. A grid assembly 927 is appropriately accommodated in front of the light source 920 for auto-focusing purposes.

It should be noted that the double-side movable planar mirror 908 can be replaced by two single-side planar movable mirrors. The dimensions of the mirror 908 (thickness and length) are defined by the predetermined plurality of incident angles, as well as by the configuration of the optical scheme, including dimensions of the beam splitter 926, etc.

The system 900 operates in the following manner. In the multi-angle illumination/detection mode, mirrors 908, 910, 912, 914 serve for sequential reflection of a light beam B emitted by the light source 902 towards the mirror 918. The position of the mirror 908 along the X-axis defines the deflector element (deflecting location) on the continuous reflecting surface of the mirror 918 on which the light beam B would impinge, and therefore defines the angle of incidence of the beam B onto the location L on the sample S. In the normal-incidence mode, the mirror 908 is in its extreme position 908', and the beam B is sequentially reflected by mirrors 908' and 910, and is then reflected by the beam splitter 926 to propagate through the opening 918A to the location L on the sample. The normally reflected beam would propagate back through the beam splitter 926 towards the detector unit 904. In the imaging mode, beam B" produced by the light source 920 is reflected from the beam splitter 924 and transmitted by the wavelength-selective mirror 910 to be further reflected from the beam splitter 926 towards the location L along the axis perpendicular to the sample's plane. A normally reflected imaging beam propagates back and is reflected by the beam splitter 926 to the CCD 922.

Figure 9:
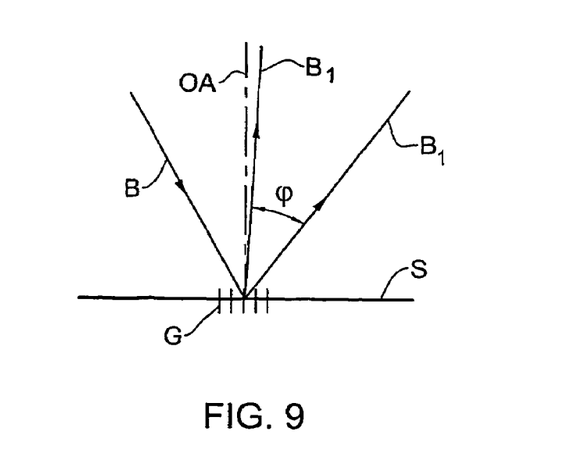
FIG. 9 illustrates how the system of the present invention can be used for measuring diffraction efficiency for the first (negative) diffraction order additionally to zero order standard measurements.

As indicated above, an imaging channel may be combined with a normal incidence illumination/detection channel. This allows for combining spectral measurements at both normal and oblique illumination in the single measurement system. In the case of spectrometry, this also allows, in some cases, for measuring diffraction efficiency for the first (negative) diffraction order additionally to zero order standard measurements. A schematic beam propagation scheme is schematically illustrated in FIG. 9. The patterned sample S has a grid G (line array). An illuminating beam B impinges onto the grid with a certain non-zero angle of incidence, and the first negative diffraction order $B_1$, angle $(-\phi)$, and a zero-order beam $B_2$ (specular reflection) can be detected. A relative angular position $(\phi)$ can be detected for each wavelength of incident light, as follows: $2 d \sin(\phi) = m\lambda$, wherein d is the period of grid, $\lambda$ is the wavelength and m is integer corresponding to the diffraction order number.

It is thus evident that the present invention provides a simple construction of an optical system having a deflector assembly with at least one movable element capable of providing variable angles of incidence and light collection with stationary mounted light source and detector. The system can be easily adjusted for additionally illuminating the same location (site) of the sample with a normal incident beam, as well as for imaging the same site.

Data indicative of the detected light is received at a control unit having a suitable data processing utility, which is operable to analyze the received data and determine at least one of the following sample's parameters: reflectivity R as a function of wavelengths or angle of incidence or both; diffraction efficiency as a function of wavelength at zero order diffraction; and typically ellipsometry measured parameters as $\Delta$, which is a change in phase of the reflected beam from the incident beam, and $\psi$, which is defined as the arctangent of the amplitude ratio of the incident and reflected beams.

Those skilled in the art will readily appreciate that various modifications and changes can be applied to the embodiments of the invention is hereinbefore exemplified without departing from its scope defined in and by the appended claims

The invention claimed is:

1. An optical system for use in measurements in a sample, the system comprising:
   (a) a light source operable to produce an incident light beam propagating in a certain direction towards the sample through an illumination channel;
   (b) a detector unit for collecting light coming from the sample through a detection channel, and generating data indicative of the collected light; and
   (c) a light directing assembly operable to direct the incident beam onto a certain location on the sample's plane with a plurality of incident angles, and to direct light returned from the illuminated location to the detector unit, the light directing assembly comprising a plurality of beam deflector elements, at least one of the deflector elements being movable, a position of said at least one movable deflector element defining a selected one of the incident angles, wherein the light directing assembly defines an additional illumination/detection channel for directing the incident beam onto the sample along an axis perpendicular to the sample's plane and directing a reflection of the perpendicular incident beam to the detector.

2. An optical system for use in measurements in a sample, the system comprising:
   (a) a light source operable to produce an incident light beam propagating in a certain direction towards the sample through an illumination channel;
   (b) a detector unit for collecting light coming from the sample through a detection channel, and generating data indicative of the collected light; and
   (c) a light directing assembly operable to direct the incident beam onto a certain location on the sample's plane with a plurality of incident angles, and to direct light returned from the illuminated location to the detector unit, the light directing assembly comprising a plurality of beam deflector elements, at least one the deflector elements being movable, a position of said at least one movable deflector element defining a selected one of the incident angles,
   wherein the plurality of said deflector elements comprises two arrays of the deflector elements, one array being located in the illumination channel and the other array being located in the detection channel,
   wherein each of the two arrays is formed by a reflecting surface of a parabolic-sector mirror, and
   wherein the light directing assembly defines an additional illumination/detection channel for directing the incident beam onto the sample along an axis perpendicular to the sample's plane and directing a reflection of the perpendicular incident beam to the detector, the additional illumination/detection channel being formed by a beam splitter spatially separating the perpendicular incident and reflected beams, and first and second planar minors, each being additionally shiftable between its operative and inoperative positions being, respectively, in and out of the optical path of the respective beam, such that when the first and second planar minors are in their operative positions, the incident and returned beams propagate through the illumination and the detection channels, respectively, and when the first and second planar mirrors are in their inoperative states, the incident and returned beams propagate through the additional illumination/detection channel.

3. An optical system for use in measurement in a sample, the system comprising:
  (a) a light source operable to produce an incident light beam propagating in a certain direction towards the sample through an illumination channel;
  (b) a detector unit for collecting light coming from the sample through a detection channel, and generating data indicative of the collected light; and
  (c) a light directing assembly operable to direct the incident beam onto a certain location on the sample's plane with a plurality of incident angles, and to direct light returned from the illuminated location to the detector unit, the light directing assembly comprising a plurality of beam deflector elements, at least one of the deflector elements being movable, a position of said at least one movable deflector element defining a selected one of the incident angles, wherein the plurality of said deflector elements comprises two arrays of the deflector elements, one array being located in the illumination channel and the other array being located in the detection channel, and wherein the light directing assembly defines an additional illumination/detection channel for directing the incident beam onto the sample along an axis perpendicular to the sample's plane and directing a reflection of the perpendicular incident beam to the detector, the additional illumination/detection channel being formed by a beam splitter spatially separating the perpendicular incident and reflected beams, and first and second planar minors, the first minor being located in the optical part of the incident beam and being shiftable between its operative and inoperative positions being, respectively, in and out of the optical path of the incident beam, and the second planar mirror being accommodated in the optical part of the returned beam and being shiftable between its operative and inoperative positions being, respectively, in and out of the optical path of the returned beam, such that when the first and second planar mirrors are in their operative positions, the incident and returned beams propagate through the illumination and the detection channels, respectively, and when the first and second planar mirrors are in their inoperative states, the incident and returned beams propagate through the additional illumination/detection channel.

* * * * *